United States Patent
De Nanteuil et al.

(10) Patent No.: US 6,716,843 B2
(45) Date of Patent: Apr. 6, 2004

(54) ALPHA-AMINO ACID SULPHONYL COMPOUNDS

(75) Inventors: Guillaume De Nanteuil, Suresnes (FR); Bernard Portevin, Elancourt (FR); Alain Benoist, Franconville (FR); Nigel Levens, Vaucresson (FR); Olivier Nosjean, Rueil-Malmaison (FR); Bernadette Husson-Robert, Nanterre (FR)

(73) Assignee: Les Laboratoires Servier, Neuilly-sur-Seine (FR)

( * ) Notice: Subject to any disclaimer, the term of this patent is extended or adjusted under 35 U.S.C. 154(b) by 107 days.

(21) Appl. No.: 10/109,407

(22) Filed: Mar. 28, 2002

(65) Prior Publication Data
US 2003/0087950 A1 May 8, 2003

(30) Foreign Application Priority Data
Mar. 28, 2001 (FR) .............................. 01 04142

(51) Int. Cl.[7] .................. A61K 31/40; A61K 31/426; C07D 295/182; C07D 277/04; C07D 207/16
(52) U.S. Cl. .................. 514/237.2; 514/365; 514/403; 514/422; 514/423; 544/141; 548/200; 548/356.1; 548/518; 548/540
(58) Field of Search .................. 544/141; 548/200, 548/356.1, 518, 540; 514/237.2, 365, 403, 422, 423

(56) References Cited
U.S. PATENT DOCUMENTS
6,201,132 B1 * 3/2001 Jenkins et al. .............. 548/535

* cited by examiner

*Primary Examiner*—Flona T. Powers
(74) *Attorney, Agent, or Firm*—The Firm of Hueschen and Sage

(57) ABSTRACT

Compound of formula (I):

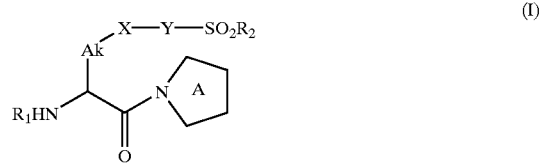

wherein:

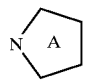

represents an optionally substituted, 5-membered, nitrogen-containing heterocycle, $R_1$ represents hydrogen, alkyl, acyl, prolyl, alanyl, histidylprolyl or phenylalanylprolyl, Ak represents an alkylene or heteroalkylene chain, X represents a single bond or optionally substituted phenylene, $R_2$ represents optionally substituted alkyl, ($C_3$–$C_{10}$) cycloalkyl, or —$NR_{2a}R_{2b}$ wherein $R_{2a}$ and $R_{2b}$, which may be the same or different, each represent hydrogen or alkyl or, together with the nitrogen atom carrying them, form a nitrogen-containing heterocycle, Y represents

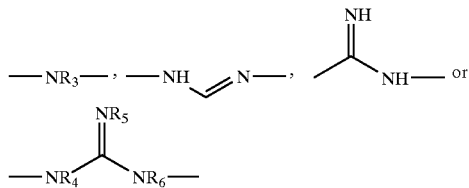

$R_3$ represents hydrogen or a group selected from alkyl, ($C_3$–$C_7$) cycloalkyl and aryl, $R_4$, $R_5$ and $R_6$, which may be the same or different, each represent hydrogen or alkyl, or $R_4$ and $R_6$, or $R_5$ and $R_6$, together with the atoms carrying them, form an imidazolidine or dihydrobenzimidazole ring, its optical isomers and addition salts thereof with a pharmaceutically acceptable acid.

Medicinal products containing the same which are useful as inhibitors of dipeptidyl-peptidase IV.

14 Claims, No Drawings

ALPHA-AMINO ACID SULPHONYL COMPOUNDS

DESCRIPTION OF THE PRIOR ART

DPP TV-inhibitors have been described in the literature, in particular amide compounds in Patent Application EP 0 490 379 and in the journal Adv. Exp. Med. Biol. 1997, 421, 157–160, and carbamate compounds in Patent Application DE 19826972.

BACKGROUND OF THE INVENTION

Dipeptidyl-peptidase IV is a membrane serine protease present in numerous human tissues and involved in numerous pathologies:

DPP IV has been shown to be responsible for inactivation of GLP-1 (glucagon-like peptide-1). GLP-1, being an important stimulator of the secretion of insulin in the pancreas, has a direct beneficial effect on the level of glucose in the blood.

Inhibition of DPP IV accordingly represents an extremely promising approach in the treatment of glucose intolerance and in disorders associated with hyperglycaemia such as, for example, non-insulin-dependent diabetes (type II diabetes) or obesity.

DPP IV has also been shown to play a part in the immune response. Expressed by T-$CD_{4+}$ lymphocytes, where it is synonymous with the antigen CD26, it plays an important part in the mechanism of transplant rejection (Transplantation 1997, 63 (10), 1495–500).

By allowing more selective suppression of the immune response, inhibition of DPP IV accordingly represents an extremely promising approach in the prevention of transplant rejection in transplant patients.

It has been also shown that endothelial DPP IV of the lung, by binding to the fibronectin of cancerous cells, promotes metastasis of those cells (J. Biol. Chem. 1998, 273 (37), 24207–24215).

DPP IV-inhibitors are accordingly useful in the treatment of cancer and the prevention of cancerous metastases.

DPP IV also plays an important part in the infection of T-$CD_{4+}$ lymphocytes by the HIV-1 virus (Res. Virol. 1997, 148 (4), 255–266). By preventing the virus from penetrating into the cells, DPP IV-inhibitors are accordingly especially promising for prevention of transmission of the HIV-1 virus. DPP IV has also been shown to be responsible for the inactivation of chemokines such as the factors SDF-1α and SDF-1β, which are known for their chemotactic and antiviral activity (Proc. Natl. Acad. Sci. USA 1998, 95 (11), 6331–6336).

DPP IV is likewise said to play an important part in the pathogenesis of periodontitis (Infect. Immun. 2000, 68 (2), 716–724).

Finally, DPP IV has been shown to be responsible for the inactivation of GLP-2, a factor facilitating recovery of the intestine after major resection (J. Surg. Res. 1999, 87 (1), 130–133).

DPP IV-inhibitors are accordingly potentially useful in recovery of the intestine.

DETAILED DESCRIPTION OF THE INVENTION

More specifically, the present invention relates to compounds of formula (I):

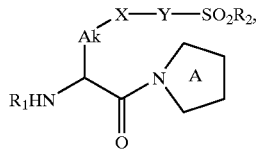

wherein:

represents a 5-membered, nitrogen-containing heterocycle optionally substituted by a cyano group, $R_1$ represents a hydrogen atom or a linear or branched ($C_1$–$C_6$)alkyl, linear or branched ($C_1$–$C_6$)acyl, prolyl, alanyl, histidylprolyl or phenylalanylprolyl group, Ak represents a linear or branched ($C_1$–$C_6$)alkylene chain or a heteroalkylene chain, X represents a single bond or a phenylene group optionally substituted by one or more identical or different groups selected from halogen atoms and linear or branched ($C_1$–$C_6$)alkyl, hydroxy, linear or branched ($C_1$–$C_6$)alkoxy and linear or branched ($C_1$–$C_6$) polyhaloalkyl groups, $R_2$ represents a linear or branched ($C_1$–$C_6$)alkyl group (optionally substituted by one or more identical or different groups selected from aryl, linear or branched ($C_1$–$C_6$)alkylsulphonyl, ($C_3$–$C_7$)cycloalkylsulphonyl, ($C_3$–$C_7$)cycloalkyl group and halogen atoms), a ($C_3$–$C_{10}$)cycloalkyl group, or —$NR_{2a}R_{2b}$, wherein $R_{2a}$ and $R_{2b}$, which may be the same or different, each represent a hydrogen atom or a linear or branched ($C_1$–$C_6$)alkyl group or, together with the nitrogen atom carrying them, form a nitrogen-containing heterocycle, Y represents a group

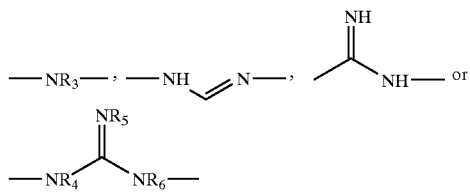

$R_3$ represents a hydrogen atom or a group selected from linear or branched ($C_1$–$C_6$) alkyl group, ($C_3$–$C_7$) cycloalkyl and aryl, $R_4$, $R_5$ and $R_6$, which may be the same or different, each represent a hydrogen atom or a linear or branched ($C_1$–$C_6$)alkyl group, or $R_4$ and $R_6$, or $R_5$ and $R_6$, together with the atoms carrying them, form an imidazolidine or dihydrobenzimidazole ring, to their optical isomers and to addition salts thereof with a pharmaceutically acceptable acid.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid, oxalic acid etc.

A nitrogen-containing heterocycle is understood to mean a saturated, monocyclic, 5- to 7-membered group containing one, two or three hetero atoms, one of those hetero atoms being the nitrogen atom and the additional hetero atom(s) optionally present being selected from oxygen, nitrogen and sulphur atoms.

Preferred nitrogen-containing heterocycles are pyrrolidinyl, thiazolidinyl, isoxazolidinyl, morpholinyl and pyrazolidinyl groups.

A heteroalkylene chain is understood to mean a linear or branched ($C_1$–$C_6$) alkylene chain wherein a —$CH_2$— member has been replaced by an oxygen or sulphur atom.

Preferred compounds of formula (I) are those wherein

represents a 1-pyrrolidinyl group optionally substituted by a cyano group, or a 1,3-thiazolidin-3-yl group optionally substituted by a cyano group.

Preferred compounds of formula (I) are those wherein X represents a single bond.

Preferred compounds of formula (I) are those wherein the configuration α to the

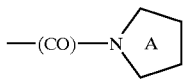

amide function is (S)

An advantageous aspect of the invention relates to compounds of formula (I) wherein $R_2$ represents a linear or branched ($C_1$–$C_6$)alkyl group and Y represents a group

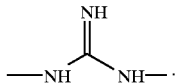

Another advantageous aspect of the invention relates to compounds of formula (I) wherein $R_2$ represents a ($C_3$–$C_{10}$) cycloalkyl group and Y represents an —NH— group.

Among the preferred compounds of the invention there may be mentioned more especially:

(S)-1-[$N^5$-{(imino)-(methylsulphonylamino)-methyl}-ornithyl]-pyrrolidine, its optical isomers and also addition salts thereof with a pharmaceutically acceptable acid;

(S)-N-[4-amino-5-oxo-5-(1-pyrrolidinyl)-pentyl]-cyclohexanesulphonamide, its optical isomers and also addition salts thereof with a pharmaceutically acceptable acid;

(2S)-2-cyano-1-[$N^6$-{(imino)-(methylsulphonylamino)-methyl}-(S)-ornithyl]-pyrrolidine, its optical isomers and also addition salts thereof with a pharmaceutically acceptable acid;

and (2S)-2-cyano-1-[$N^6$-{(imino)-(methylsulphonylamino)-methyl}-(S)-lysyl]-pyrrolidine, its optical isomers and also addition salts thereof with a pharmaceutically acceptable acid.

The invention relates also to a process for the preparation of compounds of formula (I), which process is characterised in that a compound of formula (II):

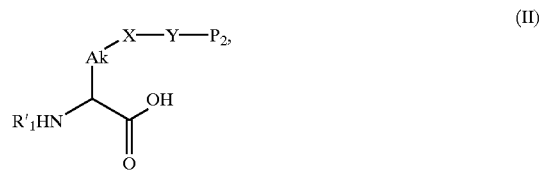

wherein Ak, X and Y are as defined for formula (I), $R'_1$ represents a protecting group for the amino function, or a linear or branched ($C_1$–$C_6$)alkyl group, a linear or branched ($C_1$–$C_6$)acyl group, a prolyl group optionally protected by an amino-function-protecting group, an alanyl group optionally protected by an amino-function-protecting group, a histidylprolyl group optionally protected by an amino-function-protecting group, or a phenylalanylprolyl group optionally protected by an amino-function-protecting group, and $P_2$ represents a hydrogen atom or a protecting group for the amino function, is reacted with a compound of formula (III):

wherein

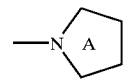

is as defined for formula (I), under conventional conditions of peptide coupling, to yield, after deprotection—where necessary—of the group Y, the compound of formula (IV):

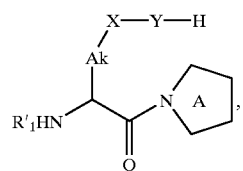

wherein

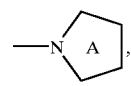

Ak, X, Y and $R'_1$ are as defined hereinbefore, which is then reacted with a compound of formula (V):

wherein $R_2$ is as defined for formula (I) and $Z_1$ represents a leaving group such as, for example, a halogen atom, to yield, after deprotection where necessary, the compound of formula (I), which is purified, where appropriate, according to a conventional purification technique, which is separated, if desired, into its optical isomers according to a conventional separation technique, and which is converted, if desired, into addition salts thereof with a pharmaceutically acceptable acid.

The compounds of formula (Ia), a particular case of the compounds of formula (I):

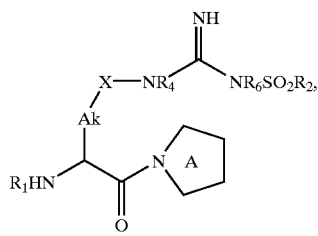

(Ia)

wherein

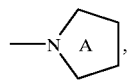

$R_1$, Ak, X, $R_2$, $R_4$ and $R_6$ are as defined for formula (I), can also be prepared by reacting a compound of formula (IIa), a particular case of the compounds of formula (II):

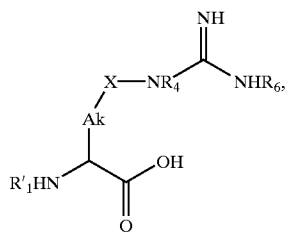

(IIa)

wherein Ak, X, $R_4$ and $R_6$ are as defined for formula (1) and $R'_1$ represents a protecting group for the amino function, or a linear or branched $(C_1-C_6)$alkyl group, a linear or branched $(C_1-C_6)$acyl group, a prolyl group optionally protected by an amino-function-protecting group, an alanyl group optionally protected by an amino-function-protecting group, a histidylprolyl group optionally protected by an amino-function-protecting group, or a phenylalanylprolyl group optionally protected by an amino-function-protecting group, with a compound of formula (V):

$$R_2-SO_2-Z_1 \qquad (V),$$

wherein $R_2$ is as defined for formula (I) and $Z_1$ represents a leaving group such as, for example, a halogen atom, to yield the compound of formula (VII):

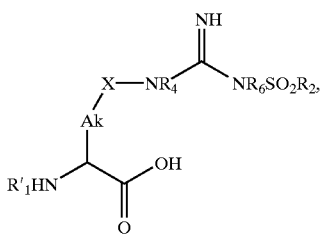

(VII)

wherein $R'_1$, Ak, X, $R_2$, $R_4$ and $R_6$ are as defined hereinbefore, which is then reacted with a compound of formula (III):

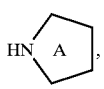

(III)

wherein

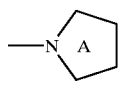

is as defined for formula (I), under conventional conditions of peptide coupling, to yield, after deprotection where necessary, the compound of formula (Ia), which is purified, where appropriate, according to a conventional purification technique, which is separated, if desired, into its optical isomers according to a conventional separation technique, and which is converted, if desired, into addition salts thereof with a pharmaceutically acceptable acid.

The compounds of formula (Ib), a particular case of the compounds of formula (I):

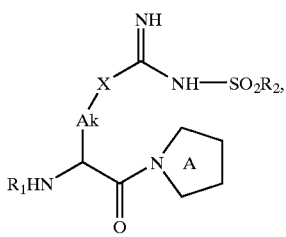

(Ib)

wherein

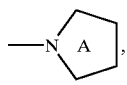

$R_1$, Ak, X and $R_2$ are as defined for formula (I), can also be prepared by reacting a compound of formula (VIII):

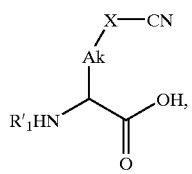
(VIII)

wherein Ak and X are as defined for formula (I) and $R'_1$ represents a protecting group for the amino function, or a linear or branched ($C_1$–$C_6$)alkyl group, a linear or branched ($C_1$–$C_6$)acyl group, a prolyl group optionally protected by an amino-function-protecting group, an alanyl group optionally protected by an amino-function-protecting group, a histidylprolyl group optionally protected by an amino-function-protecting group, or a phenylalanylprolyl group optionally protected by an amino-function-protecting group, with a compound of formula (III):

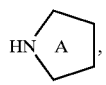
(III)

wherein

is as defied for formula (I), under conventional conditions of peptide coupling, to yield the compound of formula (IX):

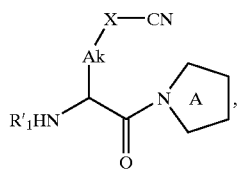
(IX)

wherein

$R'_1$, Ak and X are as defined hereinbefore, which is reacted with hydroxylamine to yield the compound of formula (X):

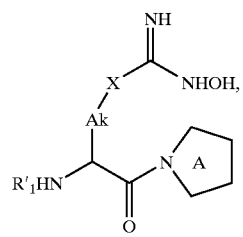
(X)

wherein

, $R'_1$, Ak and X are as defined hereinbefore, which is then reduced into the compound of formula (IVa), a particular case of the compounds of formula (IV):

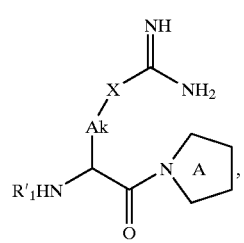
(IVa)

wherein

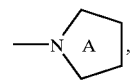, $R'_1$, Ak and X are as defined hereinbefore, which is then reacted with a compound of formula (V):

$$R_2—SO_2—Z_1 \quad (V),$$

wherein $R_2$ is as defined for formula (I) and $Z_1$ represents a leaving group such as, for example, a halogen atom, to yield, after deprotection where necessary, the compound of formula (Ib), which is purified, where appropriate, according to a conventional purification technique, which is separated, if desired, into its optical isomers according to a conventional separation technique, and which is converted, if desired, into addition salts thereof with a pharmaceutically acceptable acid.

The compounds of formula (Ic), a particular case of the compounds of formula (I):

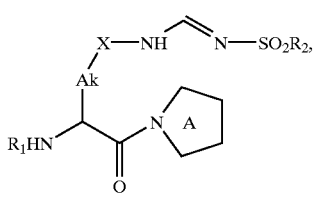

(Ic)

wherein

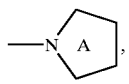, $R_1$, Ak, X and $R_2$ are as defined for formula (I), can also be prepared by reacting a compound of formula (IVb), a particular case of the compounds of formula (IV):

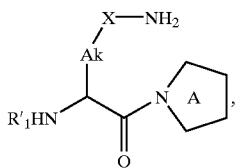

(IVb)

wherein

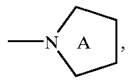,

Ak and X are as defined hereinbefore and $R'_1$ represents a protecting group for the amino function, or a linear or branched $(C_1-C_6)$alkyl group, a linear or branched $(C_1-C_6)$acyl group, a prolyl group optionally protected by an amino-function-protecting group, an alanyl group optionally protected by an amino-function-protecting group, a histidylprolyl group optionally protected by an amino-function-protecting group, or a phenylalanyl-prolyl group optionally protected by an amino-function-protecting group, with a compound of formula (XI):

$$Z_2\text{—}CH\text{=}N\text{—}SO_2R_2 \quad (XI),$$

wherein $R_2$ is as defined for formula (I) and $Z_2$ represents a leaving group such as, for example, a linear or branched $(C_1-C_6)$alkoxy group, to yield, after deprotection where necessary, the compound of formula (Ic), which is purified, where appropriate, according to a conventional purification technique, which is separated, if desired, into its optical isomers according to a conventional separation technique, and which is converted, if desired, into addition salts thereof with a pharmaceutically acceptable acid.

The compounds of formula (Id), a particular case of the compounds of formula (I):

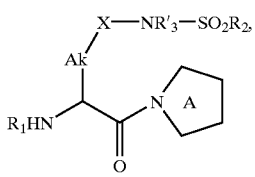

(Id)

wherein

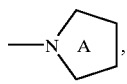, $R_1$, Ak, X and $R_2$ are as defined for formula (I) and $R'_3$ represents a group selected from linear or branched $(C_1-C_6)$alkyl, $(C_3-C_7)$ cycloalkyl and aryl, can also be prepared by reacting a compound of formula (IVb), a particular case of the compounds of formula (IV):

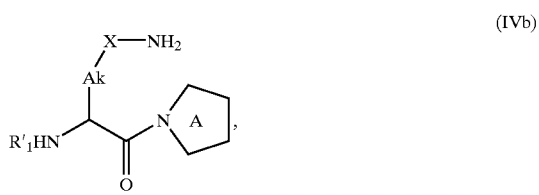

(IVb)

wherein

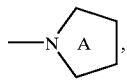,

Ak and X are as defined hereinbefore and $R'_1$ represents a protecting group for the amino function, or a linear or branched $(C_1-C_6)$alkyl group, a linear or branched $(C_1-C_6)$acyl group, a prolyl group optionally protected by an amino-function-protecting group, an alanyl group optionally protected by an amino-function-protecting group, a histidylprolyl group optionally protected by an amino-function-protecting group, or a phenylalanyl-prolyl group optionally protected by an amino-function-protecting group, with 2-nitrobenzenesulphonyl chloride to yield the compound of formula (XII):

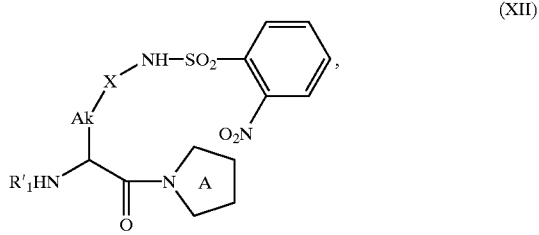

(XII)

wherein

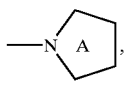

$R_1$, Ak and X are as defined hereinbefore,
which is reacted with the compound of formula (XIII):

$$R'_3\text{—OH} \tag{XIII}$$

wherein $R'_3$ is as defined hereinbefore,
in the presence of diethyl azodicarboxylate and triphenylphosphine, to yield the compound of formula (XIV):

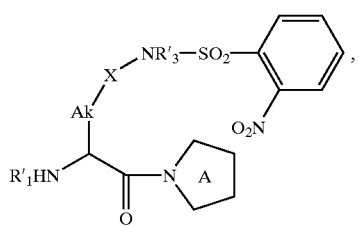 (XIV)

wherein

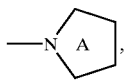

$R'_1$, Ak, X and $R'_3$ are as defined hereinbefore,
which is reacted with benzenethiol, in the presence of caesium carbonate, to yield the compound of formula (XV):

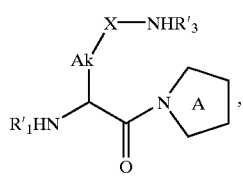 (XV)

wherein

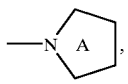

$R'_1$, Ak, X and $R'_3$ are as defined hereinbefore,
which is then reacted with a compound of formula (V):

$$R_2\text{—}SO_2\text{—}Z_1 \tag{V}$$

wherein $R_2$ is as defined for formula (I) and $Z_1$ represents a leaving group such as, for example, a halogen atom,
to yield, after deprotection where necessary, the compound of formula (Id),
which is purified, where appropriate, according to a conventional purification technique, which is separated, if desired, into its optical isomers according to a conventional separation technique, and which is converted, if desired, into addition salts thereof with a pharmaceutically acceptable acid.

The compounds of formula (Ie), a particular case of the compounds of formula (I):

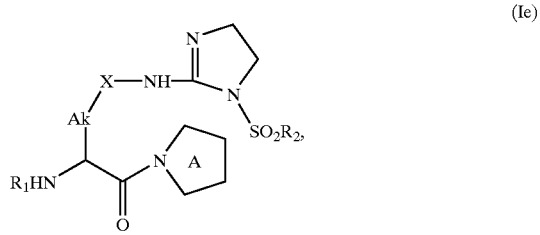 (Ie)

wherein

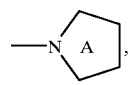

$R_1$, Ak, X and $R_2$ are as defined for formula (I),
can also be obtained by reacting the compound of formula (XVI):

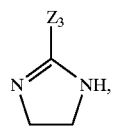 (XVI)

wherein $Z_3$ represents a leaving group such as, for example, a linear or branched $(C_1-C_6)$alkylthio group,
with a compound of formula (V):

$$R_2\text{—}SO_2\text{—}Z_1 \tag{V}$$

wherein $R_2$ is as defined for formula (I) and $Z_1$ represents a leaving group such as, for example, a hydrogen atom,
to yield the compound of formula (XVII):

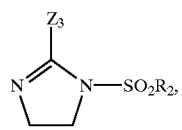 (XVII)

wherein $R_2$ and $Z_3$ are as defined hereinbefore,
which is reacted with a compound of formula (IVb), a particular case of the compounds of formula (IV):

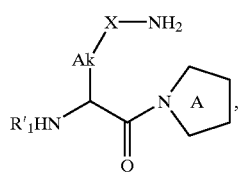 (IVb)

wherein

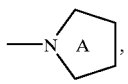

Ak and X are as defined hereinbefore and R'$_1$ represents a protecting group for the amino function, or a linear or branched (C$_1$–C$_6$)alkyl group, a linear or branched (C$_1$–C$_6$)acyl group, a prolyl group optionally protected by an amino-function-protecting group, an alanyl group optionally protected by an amino-function-protecting group, a histidylprolyl group optionally protected by an amino-function-protecting group, or a phenylalanyl-prolyl group optionally protected by an amino-function-protecting group, to yield, after deprotection where necessary, the compound of formula (Ie), which is purified, where appropriate, according to a conventional purification technique, which is separated, if desired, into its optical isomers according to a conventional separation technique, and which is converted, if desired, into addition salts thereof with a pharmaceutically acceptable acid.

Besides the fact that they are new, the compounds of the present invention have valuable pharmacological properties. They have dipeptidyl-peptidase IV-inhibiting properties, making them useful in the treatment of glucose intolerance and of disorders associated with hyperglycaemia such as type II diabetes or obesity, in the prevention of transplant rejection after transplantation, in the treatment of cancer and the prevention of cancerous metastases, in the treatment of AIDS and of periodontitis, and also in recovery of the intestine after resection.

The invention relates also to pharmaceutical compositions comprising as active ingredient at least one compound of formula (I) together with one or more inert, non-toxic, appropriate excipients. Among the pharmaceutical compositions according to the invention there may be mentioned more especially those that are suitable for oral, parenteral (intravenous, intramuscular or subcutaneous) or nasal administration, tablets or dragees, sublingual tablets, gelatin capsules, lozenges, suppositories, creams, ointments, dermal gels, injectable preparations, drinkable suspensions etc.

The useful dosage can be varied according to the nature and severity of the disorder, the administration route and also the age and weight of the patient and any associated treatments. The dosage varies from 0.5 mg to 2 g per 24 hours in one or more administrations.

The following Examples illustrate the invention but do not limit it in any way.

The starting materials used are known compounds or prepared according to known methods of preparation.

The structures of the compounds described in the Examples have been determined in accordance with the customary spectrometric techniques (infrared, NMR, mass spectrometry).

EXAMPLE 1

(S)-1-[N$^5$-{(Imino)-(methylsulphonylamino)-methyl}-ornithyl]-pyrrolidine dihydrochloride

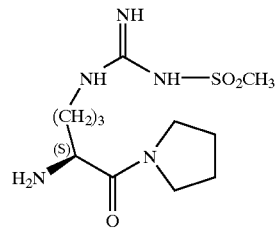

Step A: (S)-N$^2$-(Benzyloxycarbonyl)-N$^5$-{(imino)-(methylsulphonylamino)-methyl}-ornithine To 10 mmol of (S)-N$^2$-(benzyloxycarbonyl)-arginine suspended in a mixture of acetone/water 80/20 there is added, at 0° C., a sufficient amount of 4N sodium hydroxide solution to bring the pH of the reaction mixture to between 11 and 11.5. After stirring for 2 hours, there is then added a solution of methanesulphonyl chloride in acetone and then, after stirring for a further 3 hours, the mixture is neutralised using 1N hydrochloric acid solution; the acetone is then evaporated off, and the residue obtained is extracted with ether and then washed, dried, filtered and evaporated. The pale yellow oil thereby obtained is purified by chromatography over silica (eluant: dichloromethane/methanol 7/3) to yield the expected product in the form of a whitish meringue.

Step B: (S)-1-[N$^2$-(Benzyloxycarbonyl)-N$^5$-{(imino)-(methylsulphonylamino)-methyl}-ornithyl]-pyrrolidine To 10 mmol of the compound obtained in the previous Step, dissolved in dimethylformamide, there are added, at 0° C., 10 mmol of N-methyl-morpholine, and then, over the course of 10 minutes, 10 mmol of isobutyl chloroformate and finally, over the course of 10 minutes, 10 mmol of pyrrolidine dissolved in dimethylformamide. After stirring overnight at ambient temperature, the dimethylformamide is evaporated off and then sodium hydrogen carbonate solution is added to the residue obtained, which is then extracted with dichloromethane. The combined organic phases are then washed, first with 10% citric acid solution and then with water; they are then dried, filtered and evaporated. The yellow oil thereby obtained is purified by chromatography over silica (eluant: dichloromethane/methanol 95/5) to yield the expected product in the form of a whitish meringue.

Step C: (S)-1-[N$^5$-{(Imino)-(methylsulphonylamino)-methyl}-ornithyl]-pyrrolidine 10 mmol of the compound obtained in the previous Step, dissolved in ethanol, are hydrogenated in the presence of 10% palladium-on-carbon, at ambient temperature and pressure, for 6 hours. The reaction mixture is then filtered and evaporated and then, after adding water, it is lyophilised to yield the expected product.

Elemental microanalysis:

|  | C % | H % | N % | S % |
|---|---|---|---|---|
| calculated | 43.26 | 7.59 | 22.93 | 10.50 |
| found | 43.45 | 7.62 | 22.32 | 10.33 |

Step D: (S)-1-[$N^5$-{(Imino)-(methylsulphonylamino)-methyl}-ornithyl]-pyrrolidine Dihydrochloride To 10 mmol of the compound obtained in the previous Step, dissolved in dioxane, there is added a 4N solution of hydrochloric acid in dioxane. After stirring for 24 hours at ambient temperature, the solvent is evaporated off, water is added and the solution is lyophilised to yield the expected product.

Elemental microanalysis:

|  | C % | H % | N % | S % | Cl % |
|---|---|---|---|---|---|
| calculated | 34.92 | 6.67 | 18.52 | 8.47 | 18.74 |
| found | 34.42 | 6.60 | 17.78 | 8.46 | 19.52 |

EXAMPLE 2

(R)-1-[$N^5$-{(Imino)-(methylsulphonylamino)methyl}-ornithyl]-pyrrolidine dihydrochloride The expected product is obtained according to the procedure described in Example 1, replacing the (S)-$N^2$-(benzyloxycarbonyl)-arginine by (R)-$N^2$-(benzyloxycarbonyl)-arginine.

Elemental microanalysis:

|  | C % | H % | N % | S % | Cl % |
|---|---|---|---|---|---|
| calculated | 34.92 | 6.66 | 18.51 | 8.48 | 18.74 |
| found | 34.46 | 6.52 | 17.70 | 8.61 | 19.43 |

EXAMPLE 3

(S)-N-[4-Amino-5-oxo-5-(1-pyrrolidinyl)-pentyl-methane-sulphonamide hydrochloride

Step A: (S)-$N^1$-(Benzyloxycarbonyl)-$N^4$-(tert-butyloxycarbonyl)-5-oxo-5-(1-pyrrolidinyl)-1,4-pentanediamine To 10 mmol of (S)-$N^5$-(benzyloxycarbonyl)-$N^2$-(tert-butyloxycarbonyl)-ornithine dissolved in dimethylformamide there are added 10 mmol of pyrrolidine, 10 mmol of 1-hydroxybenzotriazole and 10 mmol of dicyclohexylcarbodiimide. After stirring overnight at ambient temperature, the dicyclohexylurea formed is filtered off and then the dimethylformamide is evaporated off. The chestnut-coloured oil thereby obtained is purified by chromatography over silica (eluant: dichloromethane/ethanol 95/5) to yield the expected product in the form of a yellow oil.

Step B: (S)-$N^4$-(tert-Butyloxycarbonyl)-5-oxo-5-(]-pyrrolidinyl)-1,4-pentanediamine Starting from the compound obtained in the previous Step, the expected product is obtained according to the procedure described in Step C of Example 1.

Step C: (S)-N-[4-(tert-Butyloxycarbonylamino)-5-oxo-5-(1-pyrrolidinyl)-pentyl]-methanesulphonamide To 10 mmol of the compound obtained in the previous Step, dissolved in pyridine, there are added 10 mmol of methanesulphonyl chloride dissolved in dichloromethane. After stirring overnight at ambient temperature, the solvents are evaporated off. Ethyl acetate is then added to the residue obtained, and the solution is then washed, dried, filtered and evaporated. The oil obtained is purified by chromatography over silica (eluant: dichloromethane/methanol 95/5) to yield the expected product in the form of an oil.

Step D: (S)-N-[4-Amino-5-oxo-5-(1-pyrrolidinyl)-pentyl]-methanesulphonamide Hydrochloride Starting from the compound obtained in the previous Step, the expected product is obtained according to the procedure described in Step D of Example 1.

Elemental microanalysis:

|  | C % | H % | N % | S % | Cl % |
|---|---|---|---|---|---|
| calculated | 40.06 | 7.40 | 14.02 | 10.69 | 11.82 |
| found | 39.99 | 7.75 | 13.95 | 9.81 | 13.15 |

EXAMPLE 4

(S)-1-[$N^6$-{Imino)-(methylsulphonylamino)-methyl}-lysyl]-pyrrolidine Hydrochloride

Step A: (S)-$N^5$-(tert-Butyloxycarbonyl)-6-oxo-6-(1-pyrrolidinyl)-1,5-hexanediamine Starting from (S)-$N^6$-(benzyloxycarbonyl)-$N^2$-(tert-butyloxycarbonyl)-lysine and pyrrolidine, the expected product is obtained according to the procedure described in Steps A and B of Example 3.

Step B: (S)-1-{$N^2$-(tert-Butyloxycarbonyl)-$N^6$-[(amino)-(tert-butyloxycarbonyl-imino)-methyl]-lysyl}-pyrrolidine The expected product is obtained according to the procedure described in Synthesis 1993, 579–582, by coupling of the compound obtained in the previous Step with 1-[(tert-butyloxycarbonylamino)-(tert-butyloxycarbonylimino)-methyl]-1H-pyrazole, followed by partial deprotection using acetic acid.

Step C: (S)-1-[$N^6$-{(Imino)-(methylsulphonylamino)-methyl}-lysyl]-pyrrolidine Hydrochloride Starting from the compound obtained in the previous Step, the expected product is obtained according to the procedure described in Steps C and D of Example 3.

Elemental microanalysis:

|  | C % | H % | N % | S % | Cl % |
|---|---|---|---|---|---|
| calculated | 40.50 | 7.36 | 19.68 | 9.01 | 9.96 |
| found | 40.75 | 7.50 | 19.05 | 8.63 | 10.1 |

EXAMPLE 5

(S)-N-[5-Amino-6-oxo-(1-pyrrolidinyl)-hexyl]-methane-sulphonamide

Starting from (S)-$N^6$-(benzyloxycarbonyl)-$N^2$-(tert-butyloxycarbonyl)-lysine, methane-sulphonyl chloride and pyrrolidine, the expected product is obtained according to the procedure described in Steps A to C of Example 3.

Elemental microanalysis:

|  | C % | H % | N % | S % |
|---|---|---|---|---|
| calculated | 47.63 | 8.36 | 15.15 | 11.56 |
| found | 47.54 | 8.32 | 14.21 | 11.19 |

EXAMPLE 6

(S)-N-{5-[(S)-Phenylalanyl-(S)-prolyl-amino]-6-oxo-6(1-pyrrolidinyl)-hexyl}-methanesulphonamide Hydrochloride Starting from [(S)-$N^2$-(tert-butyloxycarbonyl)-phenylalanyl]-[(S)-prolyl-]-(S)-$N^5$-(benzyl-oxycarbonyl)-lysine, methanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 53.80 | 7.22 | 12.55 | 5.74 | 6.35 |
| found | 53.77 | 7.28 | 12.24 | 5.54 | 6.56 |

EXAMPLE 7

(S)-N-{5-[(S)-Histidyl-(S)-prolyl-amino]-6-oxo-6-(1-pyrrolidinyl)-hexyl}-methanesulphonamide Dihydrochloride Starting form [(S)-$N^2$-(tert-butyloxycarbonyl)-histidyl]-[(S)-prolyl-]-(S)-$N^5$-(benzyloxy-carbonyl)-lysine, methane-sulphonyl chloride and pyrrolidine, the expected product is obtained according to the procedure described in Example 3.

EXAMPLE 8

(S)-1-[4-{[(Imino)-(methylsulphonylamino)-methyl]-amino}-phenyl-alanyl]-pyrrolidine Hydrochloride The expected product is obtained according to the procedure described in Example 4, replacing the (S)-$N^6$-(benzyloxycarbonyl)-$N^2$-(tert-butyloxycarbonyl)-lysine by (S)-4-[(tert-butyloxycarbonyl)-amino]-$N^2$-(benzyloxycarbonyl)-phenylalanine.

Elemental microanalysis:

|  | C % | H % | N % | S % | Cl % |
|---|---|---|---|---|---|
| calculated | 46.20 | 6.20 | 17.97 | 8.20 | 9.09 |
| found | 46.48 | 6.30 | 17.73 | 7.53 | 10.15 |

EXAMPLE 9

(S)-N-[2-Amino-3-oxo-3-(1-pyrrolidinyl)propyl]-methane-sulphonamide Hydrochloride Starting from (S)-3-[(benzyloxycarbonyl)-amino]-2-[(tert-butyloxycarbonyl)-amino]-propanoic acid, methane-sulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 35.35 | 6.69 | 15.47 | 11.80 | 13.04 |
| found | 34.66 | 6.56 | 14.60 | 11.84 | 14.45 |

EXAMPLE 10

(S)-N-{4-[2-Amino-3-oxo-3-(1-pyrrolidinyl)-propyl]-phenyl}-methanesulphonamide Hydrochloride Starting from (S)-4-(methylsulphonylamino)-$N^2$-(benzyloxycarbonyl)-phenylalanine, methanesulphonyl chloride and pyrrolidine, the expected product is obtained according to the procedure described in Example 1.

Elemental microanalysis:

|  | C % | H % | N % | S % | Cl % |
|---|---|---|---|---|---|
| calculated | 48.34 | 6.37 | 12.08 | 9.22 | 10.19 |
| found | 48.36 | 6.42 | 11.66 | 9.08 | 10.06 |

EXAMPLE 11

(S)-N-{[4-(2-Amino-3-oxo-3-(1-pyrrolidinyl)-propyl)phenyl]-(imino)methyl}-methanesulphonamide Hydrochloride Step A: (S)-4-[2-(tert-Butyloxycarbonylamino)-3-oxo-3-(1-pyrrolidinyl)-propyl]-benzonitrile Starting from (S)-$N^2$-(tert-butyloxycarbonyl)-4-cyanophenylalanine, methanesulphonyl chloride and pyrrolidine, the expected product is obtained according to the procedure described in Step A of Example 3.

Step B: (S)-4-[2-[(tert-Butyloxycarbonylamino]-3-oxo-3-(1-pyrrolidinyl)-propyl]-N-hydroxy-benzenecarboximidamide To 10 mmol of the compound obtained in the previous Step, dissolved in a mixture of ethanol and water, there are added 36 mmol of hydroxylamine, and then 22 mmol of potassium carbonate. The reaction mixture is then heated at reflux for 7 hours and then, after returning to ambient temperature, the solvents are evaporated off; dichloromethane and water are added, and the aqueous phase is then extracted with dichloromethane, dried, filtered and evaporated to yield the expected product in the form of a powder.

Melting point: 177° C.

Step C: (S)-4-[2-[(tert-Butyloxycarbonylamino]-3-oxo-3-(1-pyrrolidinyl)-propyl]-benzenecarboximidamide Acetate To 10 mmol of the compound obtained in the previous Step dissolved in acetic acid there are added 15 mmol of acetic anhydride and then 375 mg of 10% Pd/C. The mixture is then hydrogenated overnight at ambient temperature and pressure. After filtering off the catalyst, toluene is added and then the acetic acid is removed by azeotropic distillation. The residue obtained is then triturated in ether to yield the expected product in the form of a white powder.

Melting point: 182° C.

Step D: (S)-N-{[4-(2[(tert-Butyloxycarbonyl)-amino]-3-oxo-3-(1-pyrrolidinyl)-propyl)-phenyl]-(imino)-methyl}-methanesulphonamide After precipitation of the acetate, the compound obtained in the previous Step is dissolved in methyl isobutyl ketone, and then 30 mmol of potassium carbonate and 10 mmol of methanesulphonyl chloride are added. The reaction mixture is then heated at reflux for 2 hours and then, after returning to ambient temperature, the solvent is evaporated off; dichloromethane and water are added, the aqueous phase is extracted with dichloromethane and the organic phase is washed, dried, filtered and then evaporated. The residue obtained is purified by chromatography over silica (eluant:dichloromethane/methanol 97/3) to yield the expected product.

Step E: (S)-N-{[4-(2-Amino-3-oxo-3-(1-pyrrolidinyl)-propyl)-phenyl]-(imino)-methyl}-methanesulphonamide Hydrochloride For 10 minutes gaseous hydrogen chloride is bubbled through a solution of the compound obtained in the previous Step in ethyl acetate and then the solvent is evaporated off. The residue obtained is rinsed with ethyl acetate and then dried to yield the expected product.

EXAMPLE 12

(S)-1-[2-Amino-4-{[(imino)-(methylsulphonylamino)-methyl]-amino}-butanoyl]-pyrrolidine Hydrochloride The expected product is obtained according to the procedure described in Example 4, replacing the (S)-$N^6$-(benzyloxycarbonyl)-$N^2$-(tert-butyloxycarbonyl)-lysine by (S)-4-[(tert-butyloxycarbonyl)-amino]-2-[(benzyloxycarbonyl)-amino]-butanoic acid.

Elemental microanalysis:

|  | C % | H % | N % | S % | Cl % |
| --- | --- | --- | --- | --- | --- |
| calculated | 36.64 | 6.76 | 21.36 | 9.78 | 10.81 |
| found | 37.45 | 6.89 | 20.77 | 9.41 | 10.84 |

EXAMPLE 13

(S)-N-[3Amino-4-oxo-4-(1-pyrrolidinyl)-butyl]-methanesulphonamide Hydrochloride

Starting from (S)-4-[(benzyloxycarbonyl)-amino]-2-[(tert-butyloxycarbonyl)-amino]-butanoic acid, methanesulphonyl chloride and pyrrolidine, the expected product is obtained according to the procedure described in Example 3.

Elemental microanalysis:

|  | C % | H % | N % | S % | Cl % |
| --- | --- | --- | --- | --- | --- |
| calculated | 37.82 | 7.05 | 14.70 | 11.22 | 12.41 |
| found | 37.68 | 7.22 | 14.37 | 11.29 | 14.08 |

EXAMPLE 14

(S)-3-[$N^2$-{(Imino)(methylsulphonylamino)-methyl}-ornithyl]-1,3-thiazolidine Hydrochloride Starting from (S)-$N^2$-(benzyloxycarbonyl)-arginine, methanesulphonyl chloride and 1,3-thiazolidine, the expected product is obtained according to the procedure described in Example 1

Elemental microanalysis:

|  | C % | H % | N % | S % | Cl % |
| --- | --- | --- | --- | --- | --- |
| calculated | 33.37 | 6.16 | 19.46 | 17.82 | 9.85 |
| found | 33.87 | 6.30 | 18.74 | 18.03 | 10.34 |

EXAMPLE 15

(S)-N-[4-Amino-5-oxo-5-(1,3-thiazolidin-3-yl)-pentyl]-methane-sulphonamide Hydrochloride The expected product is obtained according to the procedure described in Example 3, replacing the pyrrolidine by 1,3-thiazolidine.

Elemental microanalysis:

|  | C % | H % | N % | S % | Cl % |
| --- | --- | --- | --- | --- | --- |
| calculated | 34.01 | 6.34 | 13.22 | 20.18 | 11.15 |
| found | 34.22 | 6.71 | 12.52 | 20.03 | 11.34 |

EXAMPLE 16

(S)-3-[$N^6$-{(Imino)-(methylsulphonylamino)-methyl}-lysyl]-1,3-thiazolidine Dihydrochloride The expected product is obtained according to the procedure described in Example 4, replacing the pyrrolidine by 1,3-thiazolidine.

Mass spectrometry: [M+H]+=338; [M−H]−=336; [M+Cl]−=372

EXAMPLE 17

(S)-N-[5-Amino-6-oxo-6(1,3-thiazolidin-3-yl)-hexyl]-methane-sulphonamide Hydrochloride Starting from (S)-$N^6$-(benzyloxycarbonyl)-$N^2$-(tert-butyloxycarbonyl)-lysine, methane-sulphonyl chloride and 1,3-thiazolidine, the expected product is obtained according to the procedure described in Example 3.

Elemental microanalysis:

|  | C % | H % | N % | S % | Cl % |
|---|---|---|---|---|---|
| calculated | 36.19 | 6.68 | 12.66 | 19.32 | 10.68 |
| found | 36.22 | 6.67 | 12.23 | 19.37 | 10.95 |

EXAMPLE 18

(S)-3-[2-Amino-3-{[(imino)-(methylsulphonylamino)-methyl]-amino}-propanoyl]-1,3-thiazolidine Hydrochloride The expected product is obtained according to the procedure described in Example 4, replacing the (S)-$N^6$-(benzyloxycarbonyl)-$N^2$-(tert-butyloxycarbonyl)-lysine by (S)-3-[(tert-butyloxycarbonyl)-amino]-2-[(benzyloxycarbonyl)-amino]-propanoic acid and the pyrrolidine by 1,3-thiazolidine.

EXAMPLE 19

(S)-N-{4-[2-Amino-3-oxo-3-(1,3-thiazolidin-3-yl)-propyl]-phenyl}-methanesulphonamide Hydrochloride Starting from (S)-3-[(benzyloxycarbonyl)-amino]-2-[(tert-butyloxycarbonyl)-amino]-propanoic acid, methane-sulphonyl chloride and 1,3-thiazolidine, the expected product is obtained according to the procedure described in Example 3.

EXAMPLE 20

(S)-3-[2-Amino-4-{[(imino)(methylsulphonylamino)-methyl]-amino}-butanoyl]-1,3-thiazolidine Hydrochloride The expected product is obtained according to the procedure described in Example 4, replacing the (S)-$N^6$-(benzyloxycarbonyl)-$N^2$-(tert-butyloxycarbonyl)-lysine by (S)-4-[(tert-butyloxycarbonyl)-amino]-2-[(benzyloxycarbonyl)-amino]-butanoic acid and the pyrrolidine by 1,3-thiazolidine.

EXAMPLE 21

(S)-N-[3-Amino-4-oxo-4-(1,3-thiazolidin-3-yl)butyl]-methane-sulphonamide Hydrochloride Starting from (S)-4-[(benzyloxycarbonyl)-amino]-2-[(tert-butyloxycarbonyl)-amino]-butanoic acid, methane-sulphonyl chloride and 1,3-thiazolidine, the expected product is obtained according to the procedure described in Example 3.

EXAMPLE 22

(S)-1-[$N^5$-{(Imino)-(ethylsulphonylamino)-methyl}-ornithyl]-pyrrolidine Hydrochloride Starting from (S)-$N^2$-(benzyloxycarbonyl)-arginine, ethanesulphonyl chloride and pyrrolidine, the expected product is obtained according to the procedure described in Example 1.

EXAMPLE 23

(S)-N-[4-Amino-5-oxo-5-(1-pyrrolidinyl)-pentyl]-ethanesulphonamide Hydrochloride Starting from (S)-$N^5$-(benzyloxycarbonyl)-$N^2$-(tert-butyloxycarbonyl)-ornithine, ethanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 42.10 | 7.71 | 13.39 | 10.22 | 11.30 |
| found | 42.31 | 7.78 | 12.47 | 9.80 | 11.18 |

EXAMPLE 24

(S)-1-[$N^5$-{(Imino)-(propylsulphonylamino)-methyl}-ornithyl]-pyrrolidine Hydrochloride Starting from (S)-$N^2$-(benzyloxycarbonyl)-arginine, propanesulphonyl chloride and pyrrolidine, the expected product is obtained according to the procedure described in Example 1.

EXAMPLE 25

(S)-N-[4-Amino-5-oxo-5-(1-pyrrolidinyl)-pentyl]-1-propanesulphonamide Hydrochloride Starting from (S)-$N^5$-(benzyloxycarbonyl)-$N^2$-(tert-butyloxycarbonyl)-ornithine, 1-propanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 43.96 | 7.99 | 12.82 | 9.78 | 10.81 |
| found | 43.91 | 7.97 | 12.44 | 9.66 | 11.64 |

EXAMPLE 26

(S)-1-[$N^5$-{(Imino)(butylsulphonylamino)-methyl}-ornithyl]-pyrrolidine Hydrochloride Starting from (S)-$N^2$-(benzyloxycarbonyl)-arginine, butanesulphonyl chloride and pyrrolidine, the expected product is obtained according to the procedure described in Example 1.

EXAMPLE 27

(S)-N-[4-Amino-5-oxo 5-(1-pyrrolidinyl)-pentyl]-butanesulphonamide Hydrochloride Starting from (S)-$N^5$-(benzyloxycarbonyl)-$N^2$-(tert-butyloxycarbonyl)-ornithine, butanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 45.67 | 8.25 | 12.29 | 9.38 | 10.37 |
| found | 45.75 | 8.17 | 12.00 | 9.04 | 10.68 |

EXAMPLE 28

(S)-1-[$N^5$-{(Imino)-(cyclopropylsulphonylamino)-methyl}-ornithyl]-pyrrolidine Hydrochloride Starting from (S)-$N^2$-(benzyloxycarbonyl)-arginine, cyclopropanesulphonyl chloride and pyrrolidine, the expected product is obtained according to the procedure described in Example 1.

EXAMPLE 29

(S)-N-[4-Amino-5-oxo-5-(1-pyrrolidinyl)-pentyl]-cyclopropane-sulphonamide Hydrochloride Starting from (S)-$N^5$-(benzyloxycarbonyl)-$N^2$-(tert-butyloxycarbonyl)-ornithine, cyclopropanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 44.23 | 7.42 | 12.90 | 9.84 | 10.88 |
| found | 44.06 | 7.83 | 12.62 | 10.06 | 10.67 |

EXAMPLE 30

(S)-1-[$N^5$-{(Imino)(cyclobutylsulphonylamino)-methyl}-ornithyl]-pyrrolidine Hydrochloride Starting from (S)-$N^2$-(benzyloxycarbonyl)-arginine, cyclobutanesulphonyl chloride and pyrrolidine, the expected product is obtained according to the procedure described in Example 1.

EXAMPLE 31

(S)-N-[4Amino-5-oxo-5-(1-pyrrolidinyl)-pentyl]-cyclobutanesulphonamide Hydrochloride Starting from (S)-$N^5$-(benzyloxycarbonyl)-$N^2$-(tert-butyloxycarbonyl)-ornithine, cyclobutanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 45.94 | 7.71 | 12.36 | 9.43 | 10.43 |
| found | 47.08 | 7.82 | 11.95 | 9.29 | 10.73 |

EXAMPLE 32

(S)-1-[$N^5$-{(Imino)-(cyclopentylsulphonylamino)methyl}-ornithyl]-pyrrolidine Hydrochloride Starting from (S)-$N^2$-(benzyloxycarbonyl)-arginine, cyclopentanesulphonyl chloride and pyrrolidine, the expected product is obtained according to the procedure described in Example 1.

EXAMPLE 33

(S)-N-[4-Amino-5-oxo-5-(1-pyrrolidinyl)-pentyl]-cyclopentanesulphonamide Hydrochloride Starting from (S)-$N^5$-(benzyloxycarbonyl)-$N^2$-(tert-butyloxycarbonyl)-ornithine, cyclopentanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 47.51 | 7.97 | 11.87 | 9.06 | 10.02 |
| found | 47.08 | 7.98 | 11.41 | 8.95 | 9.96 |

EXAMPLE 34

(S)-1-[$N^5$-{(Imino)-(cyclohexylsulphonylamino)methyl}-ornithyl]-pyrrolidine Hydrochloride Starting from (S)-$N^2$-(benzyloxycarbonyl)-arginine, cyclohexanesulphonyl chloride and pyrrolidine, the expected product is obtained according to the procedure described in Example 1.

EXAMPLE 35

(S)-N-[4-Amino-5-oxo-5-(1-pyrrolidinyl)-pentyl]-cyclohexanesulphonamide Hydrochloride Starting from (S)-$N^5$-(benzyloxycarbonyl)-$N^2$-(tert-butyloxycarbonyl)-ornithine, cyclohexanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 48.97 | 8.22 | 11.42 | 8.71 | 9.64 |
| found | 48.68 | 8.26 | 11.20 | 8.34 | 9.44 |

EXAMPLE 36

(S)-1-[3-{2-[((Imino)-(methylsulphonylamino)-methyl)amino]-ethoxy}-alanyl]-pyrrolidine Hydrochloride Starting from (S)-3-(2-{[amino-(imino)-methyl]-amino}-ethoxy)-N-(benzyloxycarbonyl)-alanine, methanesulphonyl chloride and pyrrolidine, the expected product is obtained according to the procedure described in Example 1.

EXAMPLE 37

(S)N-{2-[2-Amino-3-oxo-3-(1-pyrrolidinyl)-propoxy]-ethyl}-methanesulphonamide Hydrochloride Step A: (S)-1-{3-[2-((Benzyloxycarbonyl)-amino)-ethoxy]-N-(tert-butyloxycarbonyl)-alanyl}-pyrrolidine Starting from (S)-3-(2-{[benzyloxycarbonyl]-amino}-ethoxy)-N-(tert-butyloxycarbonyl)-alanine and pyrrolidine, the expected product is obtained according to the procedure described in Step A of Example 3.

Step B: (S)-1-{3-[2-(Amino)-ethoxy]-N-(tert-butyloxycarbonyl)-alanyl}-pyrrolidine 10 mmol of the compound obtained in the previous Step are treated with 5 g of ammonium formate and 0.7 g of 10% Pd/C in ethanol at reflux for 4 hours 30 minutes; the reaction mixture is then brought to ambient temperature and filtered. The filtrate is evaporated and the residue thereby obtained is purified by chromatography over silica (eluant: dichloromethane/methanol/ammonium hydroxide 90/10/1) to yield the expected product.

Step C: (S)-N-{2-[2-Amino-3-oxo-3-(1-pyrrolidinyl)-propoxy]-ethyl}-methanesulphonamide Hydrochloride Starting from the compound obtained in the previous Step and methanesulphonyl chloride, the expected product is obtained according to Steps C and D of Example 3.

EXAMPLE 38

(S)-1-[3-{2-[((Imino)-(methylsulphonylamino)-methyl)-amino]-ethylthio}-alanyl]-pyrrolidine Hydrochloride Starting from (S)-3-(2-{[amino-(imino)-methyl]-amino}-ethylthio)-N-(benzyloxy-carbonyl)-alanine, methanesulphonyl chloride and pyrrolidine, the expected product is obtained according to the procedure described in Example 1.

EXAMPLE 39

(S)-N-{2-[2-Amino-3-oxo-3-(1-pyrrolidinyl)-propylthio]-ethyl}-methanesulphonamide Hydrochloride Starting from (S)-3-(2-{[benzyloxycarbonyl]-amino}-ethylthio)-N-(tert-butyloxy-carbonyl)-alanine, methanesulphonyl chloride and pyrrolidine, the expected product is obtained according to the procedure described in Example 37.

Elemental microanalysis:

|  | C % | H % | N % | S % | Cl % |
|---|---|---|---|---|---|
| calculated | 36.19 | 6.68 | 12.66 | 19.32 | 10.68 |
| found | 36.17 | 6.73 | 12.19 | 18.90 | 10.82 |

EXAMPLE 40

(S)-3-[3-{2-[((Imino)-(methylsulphonylamino)-methyl)amino]-ethoxy}-alanyl]-1,3-thiazolidine Hydrochloride Starting from (S)-3-(2-{[amino-(imino)-methyl]-amino}-ethoxy)-N-(benzyloxycarbonyl)-alanine, methanesulphonyl chloride and 1,3-thiazolidine, the expected product is obtained according to the procedure described in Example 36.

EXAMPLE 41

(S)-N-{2-[2-Amino-3-oxo-3-(1,3-thiazolidin-3-yl)-propoxy]-ethyl}-methanesulphonamide Hydrochloride Starting from (S)-3-(2-{[benzyloxycarbonyl]-amino)-ethoxy)-N-(tert-butyloxycarbonyl)-alanine and 1,3-thiazolidine, the expected product is obtained according to the procedure described in Example 37.

EXAMPLE 42

(S-3-[3-{2-[((Imino)-(methylsulphonylamino)-methyl)-amino]-ethylthio]-alanyl]-1,3-thiazolidine Hydrochloride Starting from (S)-3-(2-{[amino-(imino)-methyl]-amino}-ethylthio)-N-(benzyloxycarbonyl)-alanine, methanesulphonyl chloride and 1,3-thiazolidine, the expected product is obtained according to the procedure described in Example 36.

EXAMPLE 43

(S)-N-{2-[2-Amino-3-oxo-3-(1,3-thiazolidin-3-yl) propylthio]-ethyl}-methanesulphonamide Hydrochloride Starting from (S)-3-(2-{[benzyloxycarbonyl]-amino}-ethylthio)-N-(tert-butyloxy-carbonyl)-alanine, methanesulphonyl chloride and 1,3-thiazolidine, the expected product is obtained according to the procedure described in Example 37.

EXAMPLE 44

(2S)-2-Cyano-1-[$N^5$-{(imino)-(methylsulphonylamino)-methyl}-(S)-ornithyl]-pyrrolidine Dihydrochloride Starting from (S)-$N^2$-(benzyloxycarbonyl)-arginine, methanesulphonyl chloride and (S)-2-cyano-pyrrolidine hydrochloride, the expected product is obtained according to the procedure described in Example 1.

EXAMPLE 45

N-[(4S)-4-Amino-5-oxo-5-((2S)-2-cyano-1-pyrrolidinyl)-pentyl]-methanesulphonamide Hydrochloride Starting from (S)-$N^5$-(benzyloxycarbonyl)-$N^2$-(tert-butyloxycarbonyl)-ornithine, methanesulphonyl chloride and (S)-2-cyano-pyrrolidine hydrochloride, the expected product is obtained according to the procedure described in Example 3.

Mass spectrometry: [M+H]+=289; [M−H]−=287; [M+Cl]−=322

EXAMPLE 46

(4R)-4-Cyano-3-[$N^5$-{(imino)(methylsulphonylamino)-methyl}-(S)-ornithyl]-1,3-thiazolidine Hydrochloride Starting from (S)-$N^2$-(benzyloxycarbonyl)-arginine, methanesulphonyl chloride and (R)-4-cyano-1,3-thiazolidine, the expected product is obtained according to the procedure described in Example 1.

EXAMPLE 47

N-[(4S)-4-Amino-5-oxo-54(4R)-4-cyano-1,3-thiazolidin-3-yl)-pentyl]-methanesulphonamide Hydrochloride Starting from (S)-$N^5$-(benzyloxycarbonyl)-$N^2$-(tert-butyloxycarbonyl)-ornithine, methanesulphonyl chloride and (R)-4-cyano-1,3-thiazolidine, the expected product is obtained according to the procedure described in Example 3.

EXAMPLE 48

(S)-N-({[4-Amino-5-oxo-5-(1-pyrrolidinyl)-pentyl]-amino}-methylidene)-methanesulphonamide Hydrochloride

Step A: (S)-N$^4$-(Benzyloxycarbonyl)-N$^1$-(tert-butyloxycarbonyl)-5-oxo-5-(1-pyrrolidinyl)-1,4-pentanediamine Starting from (S)-N$^2$-(benzyloxycarbonyl)-N$^5$-(tert-butyloxycarbonyl)-ornithine and pyrrolidine, the expected product is obtained according to the procedure described in Step A of Example 3.

Step B: (S)-N$^4$-(Benzyloxycarbonyl)-5-oxo-5-(1-pyrrolidinyl)-1,4-pentanediamine Hydrochloride Starting from the compound obtained in the previous Step, the expected product is obtained according to the procedure described in Step D of Example 3.

Step C: (S)-N-({[4-[(Benzyloxycarbonyl)-amino]-5-oxo-5-(1-pyrrolidinyl)-pentyl]-amino}-methylidene-methanesulphonamide To 10 mmol of the compound obtained in the previous Step, dissolved in methanol, there are added 10 mmol of potassium hydroxide dissolved in methanol. After stirring for 30 minutes at ambient temperature, the precipitate formed is filtered off, and then 10 mmol of N-(ethoxy-methylidene)-methanesulphonamide are added to the filtrate. After stirring for 15 hours at ambient temperature, the reaction mixture is evaporated and the residue obtained is purified by chromatography over silica (eluant: dichloromethane/methanol/ammonium hydroxide 97/3/0.3) to yield the expected product.

Step D: (S)-N-({[4-Amino-5-oxo-5-(1-pyrrolidinyl)-pentyl]-amino}-methylidene)-methanesulphonamide Hydrochloride Starting from the compound obtained in the previous Step, the expected product is obtained according to the procedure described in Steps C and D of Example 1.

Elemental microanalysis:

|  | C % | H % | N % | S % | Cl % |
|---|---|---|---|---|---|
| calculated | 40.42 | 7.09 | 17.14 | 9.81 | 10.85 |
| found | 39.99 | 7.38 | 16.62 | 10.27 | 10.25 |

EXAMPLE 49

(S)-1-[N$^5$-{(Imino)-(methylsulphonylamino) methyl}-N$^2$-methyl-ornithyl]-pyrrolidine Hydrochloride

Step A: (S)-1-[N$^5${(Imino)-(methylsulphonylamino)-methyl}-N$^2$-methyl-ornithyl]-pyrrolidine The expected product is obtained according to the procedure described in Steps A and B of Example 1, replacing the (S)-N$^2$-(benzyloxycarbonyl)-arginine by (S)-N$^2$-methyl-arginine.

Step B: (S)-1-[N$^5$-{(Imino)-(methylsulphonylamino)-methyl}-N$^2$-methyl-ornithyl]-pyrrolidine Hydrochloride Starting from the compound obtained in the previous Step, the expected product is obtained according to the procedure described in Step D of Example 1.

EXAMPLE 50

(S)-N-[5-Amino-1-imino-6-oxo-6-(1-pyrrolidinyl)-hexyl]-methanesulphonamide Hydrochloride The expected product is obtained according to the procedure described in Example 11, replacing the (S)-N$^2$-(tert-butyloxycarbonyl)-4-cyanophenylalanine by (S)-N$^2$-(tert-butyloxy-carbonyl)-5-cyanonorvaline.

EXAMPLE 51

(S)-N-[4-Amino-5-oxo-5-(1-pyrrolidinyl)-pentyl]-2-propanesulphonamide Hydrochloride Starting from (S)-N$^5$-(benzyloxycarbonyl)-N$^2$-(tert-butyloxycarbonyl)-ornithine, 2-propanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 43.96 | 7.99 | 12.82 | 9.78 | 10.81 |
| found | 43.96 | 8.06 | 12.42 | 9.70 | 11.30 |

EXAMPLE 52

(S)-1-[2-Amino-3-{[imino)-(methylsulphonylamino)-methyl]-amino}-propanoyl]-pyrrolidine Hydrochloride The expected product is obtained according to the procedure described in Example 4, replacing the (S)-N$^6$-(benzyloxycarbonyl)-N$^2$-(tert-butyloxycarbonyl)-lysine by (S)-3-[(tert-butyloxycarbonyl)-amino]-2-[(benzyloxycarbonyl)-amino]-propanoic acid.

Elemental microanalysis:

|  | C % | H % | N % | S % | Cl % |
|---|---|---|---|---|---|
| calculated | 34.45 | 6.42 | 22.32 | 10.22 | 11.30 |
| found | 34.51 | 6.42 | 21.35 | 10.09 | 12.30 |

EXAMPLE 53

(S)-N-[4-Amino-5-oxo-5-(1-pyrrolidinyl)-pentyl]-(cyclohexyl)-methanesulphonamide Hydrochloride Starting from (S)-N$^5$-(benzyloxycarbonyl)-N$^2$-(tert-butyloxycarbonyl)-ornithine, (cyclohexyl)-methanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 50.31 | 8.44 | 11.00 | 8.39 | 9.28 |
| found | 50.70 | 8.44 | 10.67 | 8.20 | 9.60 |

EXAMPLE 54

N-1[(5S)-5-Amino-6-oxo-6-{(2S)-2-cyano-1-pyrrolidinyl}-hexyl]-methanesulphonamide Hydrochloride Starting from (S)-$N^6$-(benzyloxycarbonyl)-$N^2$-(tert-butyloxycarbonyl)-lysine, methanesulphonyl chloride and (S)-2-cyano-pyrrolidine hydrochloride, the expected product is obtained according to the procedure described in Example 3.

Elemental microanalysis:

|  | C % | H % | N % | S % | Cl % |
|---|---|---|---|---|---|
| calculated | 42.53 | 6.84 | 16.53 | 9.46 | 10.46 |
| found | 42.82 | 6.68 | 16.02 | 9.89 | 11.37 |

EXAMPLE 55

(2S)-2-Cyano-1-[$N^6$-{(imino)-(methylsulphonylamino)-methyl}-(S)-lysyl]-pyrrolidine Hydrochloride The expected product is obtained according to the procedure described in Example 4, replacing the pyrrolidine by (S)-2-cyano-pyrrolidine hydrochloride.

Elemental microanalysis:

|  | C % | H % | N % | S % | Cl % |
|---|---|---|---|---|---|
| calculated | 40.99 | 6.62 | 22.06 | 8.42 | 9.31 |
| found | 40.70 | 6.71 | 20.91 | 8.49 | 10.30 |

EXAMPLE 56

(S)-1-[$N^6$-{1(Imino)-(methylsulphonylamino)methyl}-lysyl]-pyrazolidine Dihydrochloride The expected product is obtained according to the procedure described in Example 4, replacing the pyrrolidine by 1-(benzyloxycarbonyl)-pyrazolidine.

Mass spectrometry: [M+H]+=321; [M+Cl]−=355; [M−H]−=319

EXAMPLE 57

(4R)-4-Cyano-3-[$N^6$-{(imino)-(methylsulphonylamino)-methyl}-(S)-lysyl]-1,3-thiazolidine Hydrochloride The expected product is obtained according to the procedure described in Example 4, replacing the pyrrolidine by (R)-4-cyano-1,3-thiazolidine.

Mass spectrometry: [M+H]+=363; [M+Na]+=385; [M+K]+=401

EXAMPLE 58

N-{(5S)-5-Amino-6-oxo-6[(4R)-4-cyano-1,3-thiazolidin-3-yl]-hexyl}-methanesulphonamide Hydrochloride Starting from (S)-$N^6$-(benzyloxycarbonyl)-$N^2$-(tert-butyloxycarbonyl)-lysine, methanesulphonyl chloride and (R)-4-cyano-1,3-thiazolidine, the expected product is obtained according to the procedure described in Example 3.

Mass spectrometry: [M+H]+=321

EXAMPLE 59

(S)-N-[5-Amino-6-oxo-6-(1,3-thiazolidin-3-yl)-hexyl]-cyclohexanesulphonamide Hydrochloride Starting from (S)-$N^6$-(benzyloxycarbonyl)-N 2-(tert-butyloxycarbonyl)-lysine, cyclohexanesulphonyl chloride and 1,3-thiazolidine, the expected product is obtained according to the procedure described in Example 3.

Elemental microanalysis:

|  | C % | H % | N % | S % | Cl % |
|---|---|---|---|---|---|
| calculated | 45.04 | 7.56 | 10.50 | 16.03 | 8.86 |
| found | 45.36 | 7.37 | 10.22 | 16.69 | 9.39 |

EXAMPLE 60

(S-3-[$N^6$-{(Imino)-(cyclohexylsulphonylamino)-methyl}-lysyl]-1,3-thiazolidine Dihydrochloride The expected product is obtained according to the procedure described in Example 4, replacing the pyrrolidine by 1,3-thiazolidine and the methanesulphonyl chloride by cyclohexanesulphonyl chloride.

Elemental microanalysis:

|  | C % | H % | N % | S % | Cl % |
|---|---|---|---|---|---|
| calculated | 40.16 | 6.95 | 14.64 | 13.40 | 14.82 |
| found | 40.66 | 7.00 | 14.35 | 13.48 | 15.45 |

EXAMPLE 61

(2S)-2-Cyano-1-[$N^6$-{(imino)-(cyclohexylsulphonylamino)methyl}-(S)-lysyl]-pyrrolidine Hydrochloride The expected product is obtained according to the procedure described in Example 4, replacing the pyrrolidine by (S)-2-cyano-pyrrolidine hydrochloride and the methanesulphonyl chloride by cyclohexanesulphonyl chloride.

Mass spectrometry: [M+H]+=413

EXAMPLE 62

N-{(5S)-5-Amino-oxo-6[(4R)-4-cyano-1,3-thiazolidin-3-yl]-hexyl}-cyclohexanesulphonamide Hydrochloride Starting from (S)-$N^6$-(benzyloxycarbonyl)-$N^2$-(tert-butyloxycarbonyl)-lysine, cyclohexanesulphonyl chloride and (R)-4-cyano-1,3-thiazolidine, the expected product is obtained according to the procedure described in Example 3.

Elemental microanalysis:

|  | C % | H % | N % | S % | Cl % |
|---|---|---|---|---|---|
| calculated | 45.22 | 6.88 | 13.18 | 15.09 | 8.34 |
| found | 45.41 | 6.75 | 12.94 | 15.09 | 8.75 |

EXAMPLE 63

(4R)-4-Cyano-3-[$N^6$-{(imino)-(cyclohexylsulphonylamino)-methyl}-(S)-lysyl]-1,3-thiazolidine Dihydrochloride The expected product is obtained according to the procedure described in Example 4, replacing the pyrrolidine by (R)-4-cyano-1,3-thiazolidine and the methanesulphonyl chloride by cyclohexanesulphonyl chloride.

Mass spectrometry: [M+H]+=431

EXAMPLE 64

N-[(5S)-5-Amino-oxo-6 (2S)-2-cyano-1-pyrrolidinyl}-hexyl]-cyclohexanesulphonamide Hydrochloride Starting from (S)-$N^6$-(benzyloxycarbonyl)-$N^2$-(tert-butyloxycarbonyl)-lysine, cyclohexanesulphonyl chloride and (S)-2-cyano-pyrrolidine hydrochloride, the expected product is obtained according to the procedure described in Example 3.

Elemental microanalysis:

|  | C % | H % | N % | S % | Cl % |
|---|---|---|---|---|---|
| calculated | 50.17 | 7.68 | 13.77 | 7.88 | 8.71 |
| found | 50.25 | 7.71 | 14.07 | 7.71 | 8.31 |

EXAMPLE 65

(S)-N-[5-Amino-6-oxo-6-(1-pyrrolidinyl)-hexyl]-cyclohexanesulphonamide Hydrochloride Starting from (S)-$N^6$-(benzyloxycarbonyl)-$N^2$-(tert-butyloxycarbonyl)-lysine, cyclohexanesulphonyl chloride and pyrrolidine, the expected product is obtained according to the procedure described in Example 3.

Elemental microanalysis:

|  | C % | H % | N % | S % | Cl % |
|---|---|---|---|---|---|
| calculated | 50.31 | 8.44 | 11.00 | 8.39 | 9.28 |
| found | 50.44 | 8.44 | 10.93 | 7.99 | 9.31 |

EXAMPLE 66

(S)-N-[4-Amino-5-oxo-5-(1,3-thiazolidin-3-yl)-pentyl]-cyclohexanesulphonamide Hydrochloride The expected product is obtained according to the procedure described in Example 3, replacing the pyrrolidine by 1,3-thiazolidine and the methanesulphonyl chloride by cyclohexanesulphonyl chloride.

Elemental microanalysis:

|  | C % | H % | N % | S % | Cl % |
|---|---|---|---|---|---|
| calculated | 43.57 | 7.31 | 10.89 | 16.62 | 9.19 |
| found | 43.40 | 7.30 | 10.52 | 16.64 | 9.34 |

EXAMPLE 67

(S)-N-[4-Amino-5-oxo-5-(1-pyrrolidinyl)-pentyl]4-morpholinesulphonamide Hydrochloride The expected product is obtained according to the procedure described in Example 3, replacing the methanesulphonyl chloride by 4-morpholinesulphonyl chloride.

Elemental microanalysis:

|  | C % | H % | N % | S % | Cl % |
|---|---|---|---|---|---|
| calculated | 42.10 | 7.34 | 15.11 | 8.65 | 9.56 |
| found | 42.05 | 7.37 | 14.49 | 8.50 | 9.96 |

EXAMPLE 68

(S)-N-[5-Amino-6-oxo-(1,3-thiazolidin-3-yl)-hexyl]-N-methyl-methanesulphonamide Hydrochloride Step A: (S)-N-[5-tert-Butyloxycarbonylamino)-6-oxo-6-(1,3-thiazolidin-3-yl)-hexyl]-2-nitrobenzenesulphonamide Starting from (S)-$N^6$-(benzyloxycarbonyl)-$N^2$-(tert-butyloxycarbonyl)-lysine, 2-nitrobenzenesulphonyl chloride and 1,3-thiazolidine, the expected product is obtained according to the procedure described in Steps A to C of Example 3.

Step B: (S)-N-[5-tert-Butyloxycarbonylamino)-6-oxo-6-(1,3-thiazolidin-3-yl)-hexyl]-N-methyl-2-nitrobenzenesulphonamide To 10 mmol of the compound obtained in Step A above, dissolved in tetrahydrofuran, there are added 11.5 mmol of triphenylphosphine and 16.5 mmol of methanol. The reaction mixture is then cooled to 0° C., and 11.5 mmol of diethyl azodicarboxylate are added. The mixture is then brought to ambient temperature.

After stirring for 20 hours, the mixture is hydrolysed and extracted. The product obtained is purified by chromatography over silica (eluant: dichloromethane/ethyl acetate 80/20) to yield the expected product.

Step C: (S)-$N^1$-Methyl-$N^5$-tert-butyloxycarbonyl)-6-oxo-6-(1,3-thiazolidin-3-yl)-1,5-hexanediamine The expected product is obtained by reacting the sulphonamide obtained in Step B above with benzenethiol in the presence of caesium carbonate, according to the procedure described in Tet. Lett. 1997, 38 (33), 5831–5834.

Step D: (S)-N-[5-Amino-6-oxo-6-(1,3-thiazolidin-3-yl)-hexyl]-N-methyl-methanesulphonamide Hydrochloride Starting from the compound obtained in the previous Step and methanesulphonyl chloride, the expected product is obtained according to the procedure described in Steps C and D of Example 3.

EXAMPLE 69

(S)-N-[4-Amino-5-oxo-5-(1-pyrrolidinyl)-pentyl]-(methylsulphonyl)-methanesulphonamide Hydrochloride The expected product is obtained according to the procedure of Example 3, replacing the methanesulphonyl chloride by (methylsulphonyl)-methanesulphonyl chloride.

Elemental microanalysis:

|  | C % | H % | N % | S % | Cl % |
|---|---|---|---|---|---|
| calculated | 34.96 | 6.40 | 11.12 | 16.97 | 9.38 |
| found | 35.43 | 6.46 | 11.05 | 16.86 | 9.59 |

EXAMPLE 70

(S)-N-[4-Amino-5-oxo-5-(1-pyrrolidinyl)-pentyl]-(phenyl)-methanesulphonamide Hydrochloride The expected product is obtained according to the procedure of Example 3, replacing the methanesulphonyl chloride by (phenyl)-methanesulphonyl chloride.

Elemental microanalysis:

|  | C % | H % | N % | S % | Cl % |
|---|---|---|---|---|---|
| calculated | 51.12 | 6.97 | 11.18 | 8.53 | 9.43 |
| found | 51.00 | 7.11 | 10.44 | 7.90 | 9.26 |

EXAMPLE 71

(S)-N-[4-Amino-5-oxo-5-(1-pyrrolidinyl)-pentyl]-2,2,2-trifluoroethanesulphonamide Hydrochloride The expected product is obtained according to the procedure of Example 3, replacing the methanesulphonyl chloride by 2,2,2-trifluoroethanesulphonyl chloride.

Elemental microanalysis:

|  | C % | H % | N % | S % | Cl % |
|---|---|---|---|---|---|
| calculated | 35.92 | 5.75 | 11.42 | 8.72 | 9.64 |
| found | 35.43 | 6.07 | 11.09 | 8.70 | 9.37 |

EXAMPLE 72

(S)-N-[4-Amino-5-oxo-5(1-pyrrolidinyl)-pentyl]-sulphamide Hydrochloride

Step A: (S)-N-[4-Amino-5-oxo-5-(1-pyrrolidinyl)-pentyl]-N'-(benzyloxycarbonyl)-sulphamide To 10 mmol of chlorosulphonyl isocyanate dissolved in dichloromethane at 0° C. there are added, dropwise at 0° C., 10 mmol of benzyl alcohol dissolved in dichloromethane and then, after stirring for 1 hour 30 minutes at 0° C., 10 mmol of the compound obtained in Step B of Example 3, dissolved in a mixture of dichloromethane and triethylamine 96/4. After returning to ambient temperature, the reaction mixture is stirred overnight and then separated. The organic phase is washed, dried and evaporated to yield the expected product.

Step B: (S)-N-[4-Amino-5-oxo-5-(1-pyrrolidinyl)-pentyl]-sulphamide Hydrochloride Starting from the compound obtained in the previous Step, the expected product is obtained according to the procedure described in Steps C and D of Example 1.

Elemental microanalysis:

|  | C % | H % | N % | S % | Cl % |
|---|---|---|---|---|---|
| calculated | 35.94 | 7.04 | 18.63 | 10.66 | 11.79 |
| found | 35.92 | 6.95 | 18.18 | 11.05 | 12.35 |

EXAMPLE 73

(S)-$N^1$-[1-(Methylsulphonyl)-4,5-dihydro-1H-imidazol-2-yl]-5-oxo-5-(1-pyrrolidinyl)-1,4-pentanediamine Hydrochloride Step A: [1-(Methylsulphonyl)-2-(methylthio)-4,5-dihydro-1H-imidazole Starting from 2-(methylthio)-4,5-dihydro-1H-imidazole and methanesulphonyl chloride, the expected product is obtained according to the procedure described in Step C of Example 3.

Step B: (S)-$N^4$-(tert-Butyloxycarbonyl)-$N^1$-[1-(methylsulphonyl)-4,5-dihydro-1H-imidazol-2-yl]-5-oxo-5-(1-pyrrolidinyl)-1,4-pentanediamine To 10 mmol of the compound obtained in Step B of Example 3, dissolved in isopropanol, there are added 14.6 mmol of the compound obtained in Step A above. The reaction mixture is then heated at reflux for 48 hours. After returning to ambient temperature, hydrolysis and extraction, the product obtained is purified by chromatography over silica (eluant: dichloromethane/methanol 92.5/7.5) to yield the expected product.

Step C: (S)-$N^1$-[1-(Methylsulphonyl)-4,5-dihydro-1H-imidazol-2-yl]-5-oxo-5-(1-pyrrolidinyl)-1,4-pentanediamine Hydrochloride Starting from the compound obtained in the previous Step, the expected product is obtained according to the procedure described in Step D of Example 1.

A Mass spectrometry: [M+H]+=332; [M+Cl]−=366

EXAMPLE 74

N-[(4S)-4-Amino-5-oxo-5-((2S)-2-cyano-1-pyrrolidinyl)-pentyl]-cyclohexanesulphonamide Hydrochloride Starting from (S)-N$^5$-(benzyloxycarbonyl)-N$^2$-(tert-butyloxycarbonyl)-ornithine, cyclohexanesulphonyl chloride and (S)-2-cyano-pyrrolidine hydrochloride, the expected product is obtained according to the procedure described in Example 3.

EXAMPLE 75

(S)-N-[4-Amino-5-oxo-5-(1-pyrrolidinyl)-pentyl]-N-methyl-cyclohexanesulphonamide Hydrochloride Starting from (S)-N$^5$-(benzyloxycarbonyl)-N$^2$-(tert-butyloxycarbonyl)-ornithine, cyclohexanesulphonyl chloride and pyrrolidine, the expected product is obtained according to the procedure described in Example 68.

EXAMPLE 76

N-[(4S)-4-Amino-5-oxo-5-((2S)-2-cyano-1-pyrrolidinyl)-pentyl]-N-methyl-cyclohexanesulphonamide Hydrochloride Starting from (S)-N$^5$-(benzyloxycarbonyl)-N$^2$-(tert-butyloxycarbonyl)-ornithine, cyclohexanesulphonyl chloride and (S)-2-cyano-pyrrolidine hydrochloride, the expected product is obtained according to the procedure described in Example 68.

Pharmacological Study of Compounds of the Invention

EXAMPLE 77

Inhibition of Dipeptidyl-Peptidase IV In Vitro

The effect of the compounds on the enzymatic activity of DPP IV in vitro is evaluated as follows. The enzyme, from pig kidney, is assayed with the aid of a chromogenic substrate, glycyl-prolyl-p-nitroanilide 1.4 mM, which is hydrolysed to release p-nitroaniline, which absorbs at 405 nm. The activity of the enzyme is determined by absorbance, in the presence of variable concentrations of the compound being evaluated (mostly $10^{-4}$ to $10^{-7}$ M). The data obtained allow the effective dose for 50% inhibition of the control activity (IC$_{50}$) to be determined. The compounds of the invention have an IC$_{50}$ of from 1 nM to 20 μM.

EXAMPLE 78

Pharmaceutical Composition

| Preparation formula for 1000 tablets each containing 10 mg of active ingredient | |
|---|---|
| Compound of Example 1 | 10 g |
| Hydroxypropyl cellulose | 2 g |
| Wheat starch | 10 g |
| Lactose | 100 g |
| Magnesium stearate | 3 g |
| Talc | 3 g |

We claim:
1. A compound selected from those of formula (I):

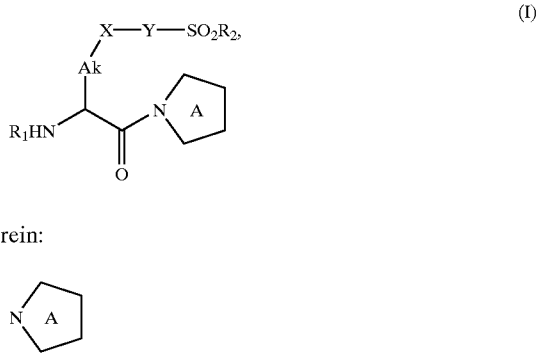

wherein:

represents a 5-membered, nitrogen-containing heterocycle optionally substituted by cyano, R$_1$ represents hydrogen, linear or branched (C$_1$–C$_6$)alkyl, linear or branched (C$_1$–C$_6$)acyl, prolyl, alanyl, histidylprolyl or phenylalanylprolyl, Ak represents a linear or branched (C$_1$–C$_6$)alkylene chain or a heteroalkylene chain, X represents a single bond or phenylene optionally substituted by one or more identical or different groups selected from halogen, linear or branched (C$_1$–C$_6$) alkyl, hydroxy, linear or branched (C$_1$–C$_6$)alkoxy and linear or branched (C$_1$–C$_6$)polyhaloalkyl, R$_2$ represents linear or branched (C$_1$–C$_6$)alkyl (optionally substituted by one or more identical or different groups selected from aryl, linear or branched (C$_1$–C$_6$) alkylsulphonyl, (C$_3$–C$_7$)cycloalkylsulphonyl, (C$_3$–C$_7$) cycloalkyl group and halogen), (C$_3$–C$_{10}$)cycloalkyl, or —NR$_{2a}$R$_{2b}$, wherein R$_{2a}$ and R$_{2b}$, which may be the same or different, each represent hydrogen or linear or branched (C$_1$–C$_6$)alkyl or, together with the nitrogen atom carrying them, form a nitrogen-containing heterocycle, Y represents

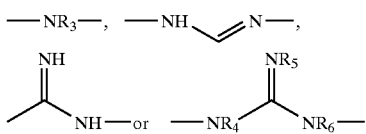

R$_3$ represents hydrogen or a group selected from linear or branched (C$_1$–C$_6$) alkyl, (C$_3$–C$_7$) cycloalkyl and aryl, R$_4$, R$_5$ and R$_6$, which may be the same or different, each represent hydrogen or linear or branched (C$_1$–C$_6$) alkyl, or R$_4$ and R$_6$, or R$_5$ and R$_6$, together with the atoms carrying them, form an imidazolidine or dihydrobenzimidazole ring, its optical isomers and addition salts thereof with a pharmaceutically acceptable acid, it being understood that a nitrogen-containing heterocycle may be a saturated, monocyclic, 5- to 7-membered group containing one, two or three hetero atoms, one of those hetero atoms being the nitrogen atom and the additional hetero atom(s) optionally present being selected from oxygen, nitrogen and sulphur atoms, and a heteroalkylene chain may be a linear or branched (C$_1$–C$_6$) alkylene chain wherein a —CH$_2$— member has been replaced by oxygen or sulphur.

2. A compound of claim 1, wherein

represents 1-pyrrolidinyl optionally substituted by cyano, or 1,3-thiazolidin-3-yl optionally substituted by cyano.

3. A compound of claim 1, wherein X represents a single bond.

4. A compound of claim 1, wherein the configuration α to the

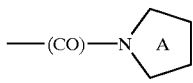

amide function is (S).

5. A compound of claim 1, wherein $R_2$ represents linear or branched $(C_1-C_6)$alkyl and Y represents,

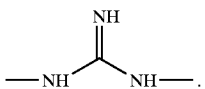

6. A compound of claim 1, wherein $R_2$ represents $(C_3-C_{10})$cycloalkyl and Y represents —NH—.

7. A compound of claim 1, which is (S)-1-[$N^5$-{(imino)-(methylsulphonylamino)-methyl}-ornithyl]-pyrrolidine.

8. A compound of claim 1, which is (S)-N-[4-amino-5-oxo-5-(1-pyrrolidinyl)-pentyl]-cyclohexanesulphonamide.

9. A compound of claim 1, which is (2S)-2-cyano-1-[$N^5$-{(imino)-(methylsulphonylamino)-methyl}-(S)-ornithyl]-pyrrolidine.

10. A compound of claim 1, which is (2S)-2-cyano-1-[$N^6$-{(imino)-(methylsulphonylamino)-methyl}-(S)-lysyl]-pyrrolidine.

11. A method for treating a living animal body afflicted with a condition requiring an inhibitor of dipeptidyl-peptidase IV, comprising the step of administering to the living animal body an amount of a compound of claim 1 which is effective for alleviation of said condition.

12. A pharmaceutical composition useful for treatment of conditions requiring an inhibitor of dipeptidyl-peptidase IV, comprising as active principle an effective amount of a compound as claimed in claim 1, together with one or more pharmaceutically acceptable excipients or vehicles.

13. A method for treating a living animal body afflicted with a condition requiring an antidiabetic agent, comprising the step of administering to the living animal body an amount of a compound of claim 1 which is effective for alleviation of said condition.

14. A pharmaceutical composition useful for treatment of type II diabetes, comprising as active principle an effective amount of a compound as claimed in claim 1, together with one or more pharmaceutically acceptable excipients or vehicles.

* * * * *